(12) United States Patent
Yi et al.

(10) Patent No.: US 9,480,632 B2
(45) Date of Patent: Nov. 1, 2016

(54) COSMETIC COMPOSITION CONTAINING INORGANIC POWDER

(71) Applicants: Seung Hwan Yi, Gyeonggi-do (KR); Min Kyung Sim, Gyeonggi-do (KR); Yeung Jin Choi, Gyeonggi-do (KR); Taek Jin Oh, Gyeonggi-do (KR); Jin Tae Han, Gyeonggi-do (KR)

(72) Inventors: Seung Hwan Yi, Gyeonggi-do (KR); Min Kyung Sim, Gyeonggi-do (KR); Yeung Jin Choi, Gyeonggi-do (KR); Taek Jin Oh, Gyeonggi-do (KR); Jin Tae Han, Gyeonggi-do (KR)

(73) Assignee: AMOREPACIFIC CORPORATION (KR)

( * ) Notice: Subject to any disclaimer, the term of this patent is extended or adjusted under 35 U.S.C. 154(b) by 0 days.

(21) Appl. No.: 14/454,690

(22) Filed: Aug. 7, 2014

(65) Prior Publication Data
US 2014/0348888 A1    Nov. 27, 2014

Related U.S. Application Data

(62) Division of application No. 13/510,747, filed as application No. PCT/KR2010/008215 on Nov. 19, 2010.

(30) Foreign Application Priority Data

Nov. 20, 2009 (KR) .................. 10-2009-0112396
Nov. 19, 2010 (KR) .................. 10-2010-0115782

(51) Int. Cl.
| | |
|---|---|
| *A61K 8/19* | (2006.01) |
| *A61K 8/02* | (2006.01) |
| *A61K 8/25* | (2006.01) |
| *A61K 8/26* | (2006.01) |
| *A61K 8/27* | (2006.01) |
| *A61K 8/29* | (2006.01) |
| *A61Q 17/04* | (2006.01) |
| *A61K 8/22* | (2006.01) |

(52) U.S. Cl.
CPC ............ *A61K 8/19* (2013.01); *A61K 8/022* (2013.01); *A61K 8/0245* (2013.01); *A61K 8/22* (2013.01); *A61K 8/25* (2013.01); *A61K 8/26* (2013.01); *A61K 8/27* (2013.01); *A61K 8/29* (2013.01); *A61Q 17/04* (2013.01); *A61K 2800/412* (2013.01)

(58) Field of Classification Search
CPC .......... A61K 8/022; A61K 8/19; A61K 8/25; A61K 2800/412
USPC ................................... 424/401, 59
See application file for complete search history.

(56) References Cited

U.S. PATENT DOCUMENTS

| | | | |
|---|---|---|---|
| 2005/0053571 A1 | 3/2005 | Hanada et al. | |
| 2005/0249762 A1 | 11/2005 | Loyd et al. | |
| 2007/0269454 A1 | 11/2007 | Maeda et al. | |
| 2008/0175805 A1 | 7/2008 | Schlemer | |
| 2009/0074686 A1 | 3/2009 | Braun et al. | |
| 2010/0129426 A1* | 5/2010 | Tanaka | A61K 33/30 424/443 |

FOREIGN PATENT DOCUMENTS

| | | |
|---|---|---|
| CN | 1127631 A | 7/1996 |
| JP | S62149613 A | 7/1987 |
| JP | S63027421 A | 2/1988 |
| JP | H11228135 A | 8/1999 |
| JP | 2000086210 A | 3/2000 |
| JP | 2001072542 A | 3/2001 |
| JP | 2001089319 A | 4/2001 |
| JP | 2004331509 A | 11/2004 |
| JP | 2005162695 A | 6/2005 |
| JP | 2006504730 A | 2/2006 |
| JP | 2006151917 A | 6/2006 |
| JP | 2006335641 A | 12/2006 |
| JP | 2007055944 A | 3/2007 |
| JP | 2008247775 A | 10/2008 |
| WO | 2009017104 A1 | 2/2009 |

OTHER PUBLICATIONS

Chinese Office Action from Chinese Patent Application No. 2010800566639.1. Date: Jan. 6, 2013.
USPTO Office Action for U.S. Appl. No. 13/510,747 dated Dec. 27, 2012.
USPTO Office Action for U.S. Appl. No. 13/510,747 dated Jun. 3, 2013.
USPTO Office Action for U.S. Appl. No. 13/510,747 dated May 9, 2014.
Japanese Office Action for Application No. JP2012-539817 dated Sep. 16, 2014.
New Cosmetic Handbook, Nikko Chemicals, Oct. 30, 2006, pp. 455-457.

\* cited by examiner

*Primary Examiner* — Johann R Richter
*Assistant Examiner* — Yanzhi Zhang
(74) *Attorney, Agent, or Firm* — Jansson Munger McKinley & Kirby Ltd.

(57) ABSTRACT

The present invention relates to a cosmetic composition comprising: (i) boron nitride; and (ii) one or more kinds of inorganic powders selected from the group consisting of cerium oxide, titanium oxide, talc, aluminum oxide, iron oxide, zinc oxide and mica. UVA, UVB and near-IR may be simultaneously screened by applying the cosmetic composition.

10 Claims, 1 Drawing Sheet

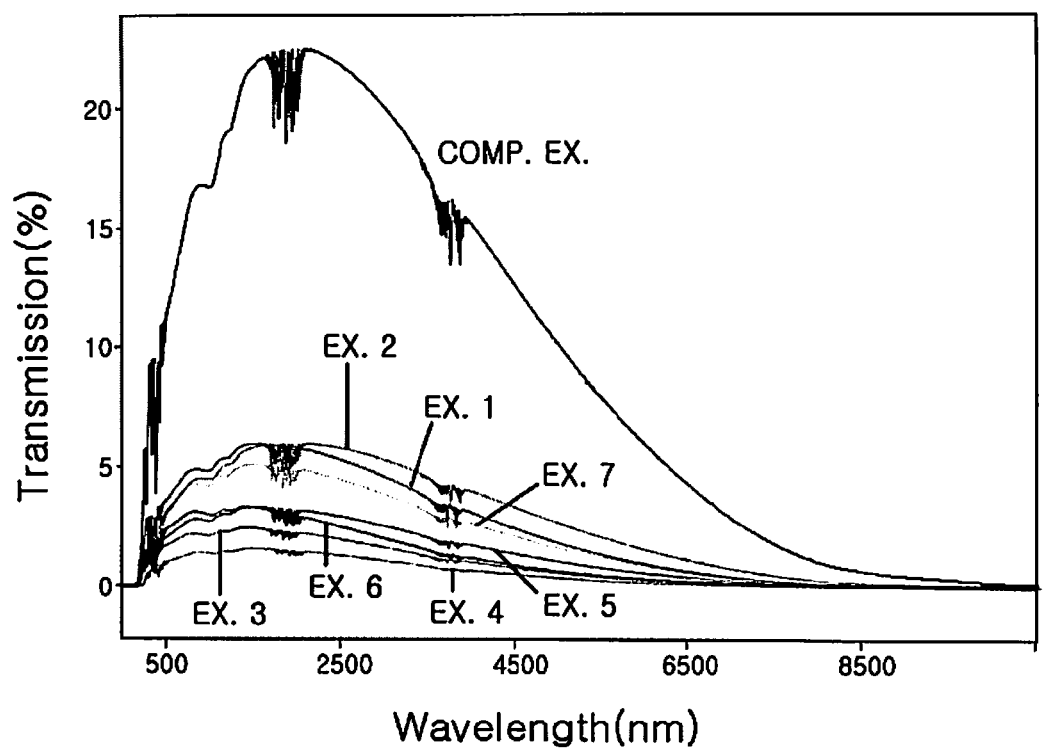

COSMETIC COMPOSITION CONTAINING INORGANIC POWDER

RELATED APPLICATIONS

This application is a divisional of U.S. patent application Ser. No. 13/510,747, filed May 18, 2012. The '747 application is a national application of International Application No. PCT/KR10/08215, filed on Nov. 19, 2010. This application also claims priority based on Korean Application No. 10-2010-0115782, filed Nov. 19, 2010 and Korean Application No. 10-2009-0112396, filed on Nov. 20, 2009. The entire contents of these applications are incorporated herein by reference.

TECHNICAL FIELD

The present disclosure relates to a cosmetic composition containing inorganic powder capable of blocking out ultraviolet rays A (UVA), UVB and near infrared rays (near-IR) that may adversely affect skin, simultaneously.

BACKGROUND ART

It is widely known that UVA (320-400 nm) and UVB (280-320 nm) having a shorter wavelength than visible light may adversely affect skin. Thus, many studies have been conducted to develop an organic or inorganic blocking agent for blocking UVA and UVB.

In addition, IR occupies 80% of sunlight, is reflected or scattered by microparticles in the atmosphere to a lower degree as compared to UV or visible light, and transmits through the atmosphere to reach the ground while not being interrupted by molecules such as oxygen or nitrogen in the atmosphere. IR is known to stimulate blood circulation in a body and to provide a hyperthermic effect, but recent studies have revealed that IR is harmful to skin, and stimulates skin wrinkle formation, for example.

IR is classified, depending on the wavelength, into near-IR having a wavelength of 780-3000 nm, IR having a wavelength of 3000-25000 nm, and far-IR having a wavelength of 25000 nm or higher. Among those, the mechanism of skin wrinkle formation caused by near-IR is different from the known mechanism of skin wrinkle formation caused by UV. As a result, in the case of exposure to sunlight including UV simultaneously with near-IR, skin aging may be accelerated even when applying the existing UV blocking agent to skin.

Therefore, there is a need for a formulation for blocking out light over a wide range of wavelengths to screen skin from UV and near-IR simultaneously.

DISCLOSURE

Technical Problem

The present disclosure is directed to providing a cosmetic composition capable of blocking out UVA, UVB and near-IR simultaneously when it is applied to skin.

Technical Solution

In one aspect, there is provided a cosmetic composition including: (i) boron nitride; and (ii) one or more kinds of inorganic powders selected from the group consisting of cerium oxide, titanium oxide, talc, aluminum oxide, iron oxide, zinc oxide and mica.

Advantageous Effects

The cosmetic composition disclosed herein blocks out UVA, UVB and near-IR simultaneously, thereby preventing skin wrinkle formation. As a result, it is possible to prevent acceleration of skin aging derived from UVA, UVB and near-IR.

DESCRIPTION OF DRAWINGS

FIG. 1 is a graph illustrating FT-IR spectra of cosmetic compositions obtained in accordance with some embodiments.

BEST MODE

As demonstrated by the following test examples, it has now been found that the cosmetic composition according to an embodiment is capable of blocking out UVA having a wavelength of 320-400 nm, UVB having a wavelength of 280-320 nm and near-IR having a wavelength of 770-1140 nm, simultaneously.

In the case of near-IR, active oxygen is generated through mitochondria, leading to a decrease in anti-oxidant content in the skin. Then, expression of matrix metalloproteinase-1 (MMP-1), a collagen-decomposing enzyme, increases, resulting in wrinkle formation. However, the cosmetic composition disclosed herein is capable of blocking out near-IR causing wrinkle formation as well as UV, and thus prevents skin wrinkle formation caused by near-IR through the above-mentioned path, thereby preventing skin aging.

The composition according to an embodiment may include boron nitride in combination with one or more kinds of inorganic powders selected from the group consisting of cerium oxide, titanium oxide, talc, aluminum oxide, iron oxide, zinc oxide and mica.

In other words, the composition according to an embodiment is capable of blocking out near-IR and UV simultaneously through the combination of boron nitride powder with 1, 2, 3, 4, 5, 6 or 7 kinds of ingredients selected from the group consisting of cerium oxide, titanium oxide, talc, aluminum oxide, iron oxide, zinc oxide and mica.

According to an embodiment, it has now been found that a cosmetic composition including: (i) boron nitride powder; and (ii) cerium oxide powder has an excellent effect of blocking out UVA, UVB and near-IR, as demonstrated by the following test examples.

According to an embodiment, boron nitride powder may have an average particle size of 1-10 μm, particularly 4-6 μm. Boron nitride powder having such an average particle size may have an excellent effect of blocking out IR.

Boron nitride powder may be present in an amount of 0.1-30 wt %, particularly 5-30 wt %, based on the total weight of the composition. When an excessively low amount of boron nitride powder is used, it is not possible to provide a sufficient effect of blocking out IR. On the other hand, when an excessively large amount of boron nitride powder is used, the resultant product may have a problem in terms of stability.

According to an embodiment, cerium oxide powder, for example, may have an average particle size of 0.1-40 μm, particularly 1-30 μm, and more particularly 5-15 μm. Cerium oxide powder having such an average particle size has an excellent effect of blocking out UVA and near-IR.

Cerium oxide powder may be present in an amount of 0.1-30 wt %, particularly 3-30 wt %, based on the total weight of the composition. When an excessively low amount of cerium oxide powder is used, it is not possible to provide a sufficient effect of blocking out UVA and near-IR. On the other hand, when an excessively large amount of cerium oxide powder is used, it is not possible to produce the composition with ease.

According to another embodiment, the composition may include: (i) boron nitride powder; and (ii) titanium oxide powder.

Titanium oxide powder may have an average particle size of 1-50 nm, particularly 10-30 nm. Titanium oxide powder having such an average particle size has an excellent effect of blocking out UVB and near-IR.

Titanium oxide powder may be present in an amount of 3-30 wt %, particularly 5-25 wt %, based on the total weight of the composition. When titanium oxide powder is used in an amount less than 5 wt %, it is not possible to provide a sufficient effect of blocking out UVB and near-IR. When titanium oxide powder is used in an amount greater than 25 wt %, the resultant product may have a problem in terms of stability on the basis of Evaluation of Functional Cosmetics Annex 4, Korea Food & Drug Administration Notice Nos. 2008-58 and 59.

According to still another embodiment, the composition may include: (i) boron nitride powder; and (ii) talc powder.

Talc powder, for example, may have an average particle size of 0.1-40 μm, particularly 5-25 μm, and more particularly 8-15 μm. Talc powder having such an average particle size has an excellent effect of blocking out IR.

Talc powder may be present in an amount of 0.1-10 wt %, particularly 3-10 wt %, based on the total weight of the composition. When an excessively low amount of talc powder is used, it is not possible to provide a sufficient effect of blocking out IR. On the other hand, when an excessively large amount of talc powder is used, the resultant product may have a problem in terms of stability.

According to still another embodiment, the composition may include: (i) boron nitride powder; and (ii) mica powder.

Mica powder, for example, may have an average particle size of 0.1-40 μm, particularly 5-40 μm, and more particularly 7-25 μm. Talc powder having such an average particle size has an excellent effect of blocking out IR.

Mica powder may be present in an amount of 0.1-10 wt %, particularly 2-8 wt %, based on the total weight of the composition. When an excessively low amount of mica powder is used, it is not possible to provide a sufficient effect of blocking out IR. On the other hand, when an excessively large amount of talc powder is used, the resultant product may have a problem in terms of stability.

According to still another embodiment, the composition may include: (i) boron nitride powder; and (ii) aluminum oxide powder.

Aluminum oxide powder, for example, may have an average particle size of 0.1-40 μm, particularly 5-15 μm, and more particularly 5-10 μm. Aluminum oxide powder having such an average particle size has an excellent effect of blocking out IR.

Aluminum oxide powder may be present in an amount of 3-15 wt %, particularly 2-8 wt %, based on the total weight of the composition. When an excessively low amount of aluminum oxide powder is used, it is not possible to provide a sufficient effect of blocking out IR. On the other hand, when an excessively large amount of aluminum oxide powder is used, the resultant product may have a problem in terms of stability.

According to still another embodiment, the composition may include: (i) boron nitride powder; and (ii) zinc oxide powder.

Zinc oxide powder, for example, may have an average particle size of 0.1-40 μm, particularly 0.3-5 μm, and more particularly 0.3-1.5 μm. Zinc oxide powder having such an average particle size has an excellent effect of blocking out IR.

Zinc oxide powder may be present in an amount of 1-20 wt %, particularly 1-15 wt %, based on the total weight of the composition. When an excessively low amount of zinc oxide powder is used, it is not possible to provide a sufficient effect of blocking out IR. On the other hand, when an excessively large amount of zinc oxide powder is used, the resultant product may have a problem in terms of stability.

According to yet another embodiment, the composition may include: (i) boron nitride powder; and (ii) iron oxide powder.

Iron oxide powder, for example, may have an average particle size of 0.1-40 μm, particularly 0.1-10 μm, and more particularly 0.2-7 μm. Iron oxide powder having such an average particle size has an excellent effect of blocking out IR.

Iron oxide powder may be present in an amount of 0.001-5 wt %, particularly 0.001-2 wt %, based on the total weight of the composition. When an excessively low amount of iron oxide powder is used, it is not possible to provide a sufficient effect of blocking out IR. On the other hand, when an excessively large amount of iron oxide powder is used, the resultant product may have a problem in terms of stability.

The cosmetic composition disclosed herein may be formulated into various forms without particular limitation. For example, the cosmetic composition disclosed herein may be formulated into skin softeners, nourishing lotion, nourishing cream, massage cream, pack, sun cream, foundation or makeup base. In each formulation, additional ingredients other than the essential ingredients may be selected and admixed suitably by those skilled in the art depending on the use and purpose.

MODE FOR INVENTION

The examples and test examples will now be described. The following examples and test examples are for illustrative purposes only and not intended to limit the scope of the present disclosure.

Comparative Example and Examples 1-7

Water-in-oil type make-up cosmetic compositions according to Comparative Example and Examples 1-7 are provided by using the compositions as shown in the following Table 1. Each composition is obtained as follows.

The oil phase ingredients are mixed with colorants to form a dispersion.

All of the water phase ingredients are mixed together to form a mixture.

The mixture is added gradually to the dispersion obtained mentioned above, followed by mixing and complete deaeration, to provide a water-in-oil type make-up cosmetic composition.

TABLE 1

| Ingredients | Compound | Comp. Ex. | Ex. 1 | Ex. 2 | Ex. 3 | Ex. 4 | Ex. 5 | Ex. 6 | Ex. 7 |
|---|---|---|---|---|---|---|---|---|---|
| Oil phase ingredients | Decamethylcyclopentasiloxane | 15.00 | 15.00 | 15.00 | 15.00 | 15.00 | 15.00 | 15.00 | 15.00 |
| | Dicaprylyl carbonate | 10.00 | 10.00 | 10.00 | 10.00 | 10.00 | 10.00 | 10.00 | 10.00 |
| | Ethylhexylmethoxy cinnamate | 10.00 | 10.00 | 10.00 | 10.00 | 10.00 | 10.00 | 10.00 | 10.00 |
| | Cetyl dimethicone copolyol (surfactant) | 1.00 | 1.00 | 1.00 | 1.00 | 1.00 | 1.00 | 1.00 | 1.00 |
| | Distearammonium hectorite | 1.00 | 1.00 | 1.00 | 1.00 | 1.00 | 1.00 | 1.00 | 1.00 |
| | Paraoxybenzoic ester | q.s. | q.s. | q.s. | q.s. | q.s. | q.s. | q.s. | q.s. |
| Colorant | Boron nitrite | — | 5.00 | 5.00 | 5.00 | 5.00 | 5.00 | 5.00 | 5.00 |
| | Aluminum oxide | — | 5.00 | — | — | — | — | — | — |
| | Zinc Oxide | — | — | 5.00 | — | — | — | — | — |
| | Titanium oxide | — | — | — | 5.00 | — | — | — | — |
| | Cerium oxide | — | — | — | — | 5.00 | — | — | — |
| | Iron oxide | — | — | — | — | — | 5.00 | — | — |
| | Talc | — | — | — | — | — | — | 5.00 | — |
| | Mica | — | — | — | — | — | — | — | 5.00 |
| Water phase ingredients | Purified water | To 100 | To 100 | To 100 | To 100 | To 100 | To 100 | To 100 | To 100 |
| | Disodium EDTA | 0.05 | 0.05 | 0.05 | 0.05 | 0.05 | 0.05 | 0.05 | 0.05 |
| | Sodium chloride | 1.00 | 1.00 | 1.00 | 1.00 | 1.00 | 1.00 | 1.00 | 1.00 |
| | Phenoxy ethanol | q.s. | q.s. | q.s. | q.s | .q.s. | q.s. | q.s. | q.s. |

Test Example 1

Test for Determining Effect of Blocking Out Near-IR

The make-up cosmetic compositions obtained from Comparative Example and Examples 1-7 are evaluated for their effects of blocking out near-IR in the manner as described hereinafter.

In this test, the effect of blocking out near-IR of each of the compositions according to Examples 1-7 is compared with that of Comparative Example as a negative control. The results are shown in FIG. 1. FIG. 1 is a graph illustrating effects of blocking out near-IR determined by Fourier Transform Near-Infrared Spectrometer (MB 100 available from ABB Co.). Near-IR has a wavelength of 770-1400 nm. A lower transmission in this wavelength range suggests a higher effect of blocking out near-IR.

Referring to FIG. 1, it can be seen that boron nitride with titanium oxide (Ex. 3), boron nitride with cerium oxide (Ex. 4), and boron nitride with talc (Ex. 6) show the highest effect of blocking out light in a wavelength range corresponding to near-IR.

Test Example 2

Test for Determining Effect of Blocking Out UV

The compositions obtained from Comparative Example and Examples 1-7 are evaluated for their sun protection factors, and the results are shown in the following Table 2. An SPF Analyzer (Optometrics USA, SPF290S) is used to determine the sun protection factor (SPF) and protection of UVA (PFA). SPF means an index showing an effect of blocking out UVB, while PFA means an index showing an effect of blocking out UVA.

TABLE 2

| | In-vitro SPF | In-vitro PFA |
|---|---|---|
| Comp. Ex. | 10.1 | 2.1 |
| Ex. 1 | 11.2 | 2.2 |
| Ex. 2 | 13.0 | 3.7 |
| Ex. 3 | 16.8 | 2.6 |
| Ex. 4 | 16.6 | 3.0 |
| Ex. 5 | 11.7 | 2.9 |
| Ex. 6 | 13.6 | 2.7 |
| Ex. 7 | 11.4 | 2.6 |

Referring to Table 2, it can be seen that the SPF index of each of the compositions according to Examples 1 to 7 is higher than the SPF index of Comparative Example. Particularly, it is shown that boron nitride with titanium oxide (Ex. 3), boron nitride with cerium oxide (Ex. 4), and boron nitride with talc (Ex. 6) show the highest SPF index. In addition, boron nitride with zinc oxide (Ex. 2) shows the highest PFA index.

Based on the results of Test Examples 1 and 2, it is shown that a cosmetic composition including: (i) boron nitride; and (ii) one or more kinds of inorganic powders selected from the group consisting of cerium oxide, titanium oxide and talc, may be used as a cosmetic composition for blocking out UVA, UVB and near-IR.

Hereinafter, some formulation examples will be explained but the following formulation examples are for illustrative purposes only and not intended to limit the scope of the present disclosure.

Formulation Example 1

Skin Softener (Skin Lotion)

Skin softener is obtained in a conventional manner according to the composition as shown in the following Table 3.

TABLE 3

| Ingredient | Amount (wt %) |
| --- | --- |
| Purified water | Balance |
| Example 3 | 5.0 |
| Ethylenediamine tetraacetic acid | 0.02 |
| Glycerin | 5 |
| Butylene glycol | 3 |
| PEG/PPG-17/6 copolymer | 3 |
| Ethanol | 5 |
| Polyoxyethylene hydrogenated castor oil | 0.4 |
| Methyl paraben | 0.1 |
| Fragrance | 0.1 |
| Preservative, pigment and perfume | q.s. |

Formulation Example 2

Nourishing Lotion (Milk Lotion)

Nourishing lotion is obtained in a conventional manner according to the composition as shown in the following Table 4.

TABLE 4

| Ingredient | Amount (wt %) |
| --- | --- |
| Purified water | Balance |
| Example 4 | 5.0 |
| Bees wax | 4.0 |
| Polysorbate 60 | 1.5 |
| Sorbitan sesquioleate | 1.5 |
| Liquid paraffin | 0.5 |
| Caprylic/capric triglyceride | 5.0 |
| Glycerin | 3.0 |
| Butylene glycol | 3.0 |
| Propylene glycol | 3.0 |
| Carboxyvinyl polymer | 0.1 |
| Triethanolamine | 0.2 |
| Preservative, pigment and perfume | q.s. |

Formulation Example 3

Nourishing Cream

Nourishing cream is obtained in a conventional manner according to the composition as shown in the following Table 5.

TABLE 5

| Ingredient | Amount (wt %) |
| --- | --- |
| Purified water | Balance |
| Example 3 | 5.0 |
| Bees wax | 10.0 |
| Polysorbate 60 | 1.5 |
| PEG60 cured castor oil | 2.0 |
| Sorbitan sesquioleate | 0.5 |
| Liquid paraffin | 10.0 |
| Squalane | 5.0 |
| Caprylic/capric triglyceride | 5.0 |
| Glycerin | 5.0 |
| Butylene glycol | 3.0 |
| Propylene glycol | 3.0 |
| Triethanolamine | 0.2 |
| Preservative, pigment and perfume | q.s. |

Formulation Example 4

Massage Cream

Massage cream is obtained in a conventional manner according to the composition as shown in the following Table 6.

TABLE 6

| Ingredient | Amount (wt %) |
| --- | --- |
| Purified water | Balance |
| Example 4 | 5.0 |
| Bees wax | 10.0 |
| Polysorbate 60 | 1.5 |
| PEG60 cured castor oil | 2.0 |
| Sorbitan sesquioleate | 0.8 |
| Liquid paraffin | 40.0 |
| Squalane | 5.0 |
| Caprylic/capric triglyceride | 4.0 |
| Glycerin | 5.0 |
| Butylene glycol | 3.0 |
| Propylene glycol | 3.0 |
| Triethanolamine | 0.2 |
| Preservative, pigment and perfume | q.s. |

Formulation Example 5

Pack

Pack is obtained in a conventional manner according to the composition as shown in the following Table 7.

TABLE 7

| Ingredient | Amount (wt %) |
| --- | --- |
| Purified water | Balance |
| Example 3 | 5.0 |
| Polyvinyl alcohol | 13.0 |
| Sodium carboxymethyl cellulose | 0.2 |
| Glycerin | 5.0 |
| Allantoin | 0.1 |
| Ethanol | 6.0 |
| PEG-12 nonyl phenyl ether | 0.3 |
| Polysorbate 60 | 0.3 |
| Preservative, pigment and perfume | q.s. |

While the exemplary embodiments have been shown and described, it will be understood by those skilled in the art that various changes in form and details may be made thereto without departing from the spirit and scope of the present disclosure as defined by the appended claims.

The invention claimed is:

1. A method for simultaneously blocking out ultraviolet (UV) rays and near-infrared (near-IR) rays having a wavelength of 770-1140 nm comprising administering an effective amount of a cosmetic composition comprising:
   (I) 5-30 wt % of boron nitride based on the total weight of the composition; and
   (II) one or more inorganic powders selected from the group consisting of cerium oxide, titanium oxide, talc, aluminum oxide, iron oxide, zinc oxide and mica to a subject in such need, wherein the titanium oxide powder has an average particle size of 1-50 nm, and the cosmetic composition does not include a polymer having a phosphorylcholine residue.

2. The method according to claim 1 wherein boron nitride powder has an average particle size of 1-10 μm.

3. The method according to claim 1 wherein one or more inorganic powders selected from the group consisting of cerium oxide, talc, aluminum oxide, iron oxide, zinc oxide and mica have an average particle size of 0.1-40 μm.

4. The method according to claim 1 wherein cerium oxide powder is present in an amount of 0.1-30 wt % based on the total weight of the composition.

5. The method according to claim 1 wherein titanium oxide powder is present in an amount of 5-25 wt % based on the total weight of the composition.

6. The method according to claim 1 wherein talc powder is present in an amount of 0.1-10 wt % based on the total weight of the composition.

7. The method according to claim 1 wherein aluminum oxide powder is present in an amount of 3-15 wt % based on the total weight of the composition.

8. The method according to claim 1 wherein iron oxide powder is present in an amount of 0.001-5 wt % based on the total weight of the composition.

9. The method according to claim 1 wherein zinc oxide powder is present in an amount of 1-20 wt % based on the total weight of the composition.

10. The method according to claim 1 wherein mica powder is present in an amount of 0.1-10 wt % based on the total weight of the composition.

\* \* \* \* \*